(12) United States Patent
Basler et al.

(10) Patent No.: US 6,614,538 B1
(45) Date of Patent: Sep. 2, 2003

(54) METHOD AND APPARATUS FOR RECORDING MEDICAL OBJECTS, IN PARTICULAR FOR RECORDING MODELS OF PREPARED TEETH

(75) Inventors: Franz Basler, Laudenbach (DE); Thomas Hasenzahl, Darmstadt (DE); Joachim Pfeiffer, Bensheim (DE); Axel Schwotzer, Gross-Gerau (DE)

(73) Assignee: Sirona Dental Systems GmbH, Bensheim (DE)

( * ) Notice: Subject to any disclaimer, the term of this patent is extended or adjusted under 35 U.S.C. 154(b) by 128 days.

(21) Appl. No.: 09/690,754

(22) Filed: Oct. 18, 2000

(30) Foreign Application Priority Data

Oct. 21, 1999 (DE) .......................................... 199 50 780

(51) Int. Cl.⁷ .............................. G01B 11/24; A61C 1/00
(52) U.S. Cl. ........................ 356/602; 356/623; 433/29; 433/233
(58) Field of Search ................................ 356/601, 602, 356/606, 607, 614, 615, 622, 623; 250/559.21, 559.22, 559.24; 433/29, 24, 4, 44, 68, 2, 3, 223

(56) References Cited

U.S. PATENT DOCUMENTS

| | | | | |
|---|---|---|---|---|
| 4,184,175 A | * | 1/1980 | Mullane, Jr. .................. 348/66 |
| 4,575,805 A | * | 3/1986 | Moermann et al. .......... 700/163 |
| 4,721,388 A | * | 1/1988 | Takagi et al. ................ 356/376 |
| 4,764,012 A | * | 8/1988 | Ryden et al. ................ 356/347 |
| 4,838,696 A | * | 6/1989 | Pryor .......................... 356/375 |
| 5,051,823 A | * | 9/1991 | Cooper et al. ................ 348/66 |
| 5,291,270 A | * | 3/1994 | Koch et al. .................. 356/375 |
| 5,369,490 A | * | 11/1994 | Kawai et al. ................ 356/376 |
| 5,424,836 A | | 6/1995 | Weise et al. ................. 356/376 |
| 5,521,707 A | * | 5/1996 | Castore et al. .............. 356/394 |
| 5,548,405 A | * | 8/1996 | Motosugi ..................... 356/376 |
| 5,671,055 A | * | 9/1997 | Whittlesey et al. .......... 356/376 |
| 5,671,056 A | * | 9/1997 | Sato ............................ 356/376 |
| 5,737,085 A | * | 4/1998 | Zollars et al. ............... 356/376 |
| 5,760,906 A | * | 6/1998 | Sato ............................ 356/376 |
| 6,086,366 A | * | 7/2000 | Mueller et al. ................ 433/29 |

FOREIGN PATENT DOCUMENTS

| | | |
|---|---|---|
| EP | 0 455 855 B1 | 4/1995 |
| EP | 0 671 679 B1 | 1/2000 |

OTHER PUBLICATIONS

Scheimpflug Imaging, by Anna K. Junk, MD, Sep. 21, 2000.
Principles of View Camera Focus, by Harold M. Merklinger, May 1996.
Dental CAD/CAM GN–I, undated.

* cited by examiner

*Primary Examiner*—Hoa Q. Pham
(74) *Attorney, Agent, or Firm*—Dykema Gossett PLLC

(57) ABSTRACT

An apparatus for recording medical objects, in particular for recording models of prepared teeth, comprising a position-sensitive sensor (2), which is movable in the projection direction, with a projection unit and a receiving unit (13-15; 18-21), and with a certain triangulation angle ($\alpha$) located between the projection path of the rays (10) of the projection unit (13-15) and the observation path of the rays (11) of the receiving unit (18-21), and with the projection path of the rays (10) aligned parallel to the direction of movement of the sensor (2), is realized for the accurate recording action of edges and steep surfaces of the type that occur in tooth cavities with a triangulation angle ($\alpha$) that is smaller than 10°, preferably smaller than 5°.

11 Claims, 3 Drawing Sheets

METHOD AND APPARATUS FOR RECORDING MEDICAL OBJECTS, IN PARTICULAR FOR RECORDING MODELS OF PREPARED TEETH

BACKGROUND OF THE INVENTION

The invention relates to an apparatus and to a method for recording medically prepared teeth, in particular tooth models. Tooth models are characterized by steep walls and filigree structures and can include narrow and deep holes. Furthermore, when measuring tooth models it is necessary to record edges and steep surfaces with precision.

The measurement of a tooth model according to the triangulation procedure with a certain parallax angle, which is as small as possible, between the projection path of the rays and the observation path of the rays is known from EP-A-0 455 855. During the measuring process the model undergoes helical scanning by a triangulation sensor arranged in a stationary position and set to reveal sufficient detail. Also known in the art is the practice to mount this optical measuring instrument on one of the tool support heads allowing the sensor to be brought into the best possible measuring position by way of defined movements. The tool spindle movements are known and can be superimposed over the actual measured values of the sensor as a correction. A focus detection sensor is proposed as an example for a sensor to be used. The type and design of the measuring method remains unspecified.

Known from the "Dental CAD/CAM GM-I" brochure, authored by the GC Corporation of Tokyo, is the measuring of a tooth restoration in which a laser is able to measure said tooth restoration using a 5-axis measurement. The measuring unit is a separate component of a machine group for producing tooth restorations which further includes a separate grinding machine and a computer for process control.

SUMMARY OF THE INVENTION

It is the objective of the invention to measure medical objects, in particular to measure models of prepared teeth, in a simple manner.

An apparatus for recording medical objects, in particular for recording models of prepared teeth, is devised in accordance with the invention as comprising a position-sensitive sensor that is movable in the projection direction comprising a projection unit and a receiving unit; and between the projection path of the rays of the projection unit and the observation path of the rays of the receiving unit there is a certain triangulation angle, while the projection path of the rays is aligned parallel to the moving direction of the sensor. Since the triangulation angle is less than 10°, and preferably less than 5°, it is possible to measure with sufficient accuracy inside the tooth cavities allowing for the exact recording of edges and steep surfaces. Due to the fact that the receiving unit has a strip comprising several pixels, which are adjacent to each other and which can be evaluated individually, acting in conjunction with the signal processing, it is possible to take into account double reflections and divergence of the light spot at the edges when determining the ray's center of gravity. Thus, the disadvantages of the otherwise widely used position-sensitive sensors (PSD=position-sensitive device) can be avoided. CCDs or photodiodes limiting the determination of the ray's center of gravity to the calculation of only few pixels are advantageous. In order to be able to make adjustments for alignment errors of the observation path of the rays in relation to the strip on the receiving unit a medium allowing the divergence of the ray is arranged in a direction that is perpendicular to the strip. The sensor is movable in the projection direction to such an extent that it measures, with respect to the measuring accuracy, the same object point while moving in the projection direction.

If media for redirecting the path of the rays are arranged in the projection path of the rays and/or the observation path of the rays it is still possible to make enough room for the apparatus comprising the projection unit and the receiving unit despite the small triangulation angle.

Because the sensor is movable in the projection direction it is sufficient if the measuring range of the sensor covers at the most one tenth of the largest possible object dimensions to be measured in the projection direction.

It is advantageous if the projection unit comprises a laser diode with collimator optics and a selector of the laser diode with the radiation capacity being controlled by way of a pulse width modulated selector (PWM) whose pulse duty factor is calculated on the basis of the signal of the receiver. Pulse width modulation refers to the average laser intensity being adjusted by way of the time ratio between switched on laser and switched off laser.

The collimator optic comprises lenses that focus the laser beam on a certain point.

Another feature of the invention is an apparatus for recording medical objects with the sensor arranged inside a housing. Envisioned in the housing is a window for the projection path of the rays and/or the observation path of the rays with the window being heated to a higher temperature than the ambient temperature.

An apparatus of this type can be advantageously arranged inside a grinding chamber of a grinding machine on a spindle motor and in close thermal contact with the motor. Due to the close thermal contact with the spindle motor, which is the main source of heat during the grinding process, the window assumes for the most part the spindle motor's temperature, which means that even in moist, warm conditions are prevalent inside the chamber of the grinding machine a fogging up of the window, and thereby a falsification of the measures values of the sensor, is avoided.

Using two receiving units will improve the measuring accuracy in particular with regard to the measuring of the edges. For this purpose it is advantageous to arrange the two receiving units symmetrically in relation to the projection path of the rays in order to compensate for the asymmetrical geometry of the triangulation procedure. With regard to the receiver signals it is, respectively, the more meaningful signal, e.g. in terms of its higher intensity or a clearer focus image, that is given more weight. Even though the compactness has to be sacrificed with the additional observation path of the rays, the enhanced measurement can take priority over compactness in special applications.

Another feature of the invention is a method for measuring medical objects, in particular for measuring tooth models, and the measuring is carried out according to the triangulation procedure with a certain triangulation angle between the projection path of the rays and the observation path of the rays. It is possible to compensate for the disadvantages resulting from the small triangulation angle because in a first step a sensor is moved in the projection direction by a drive apparatus in such a way that the object to be measured is brought inside an area +/−B which is part of a working distance a; and in a second step the sensor is moved along the object that is to be measured; and in a third step a measuring signal generated by the sensor is checked in order to determine if the signal is inside a range +/−B in relation to the working distance a; and in a forth step, if a measuring value is outside of the range B, the position of the sensor is modified to the extent that the sensor comes to be in the range +/−B, which means that preferably the working distance a is achieved; and in a fifth step a measuring value is generated, subsequently the object position is calculated based on the movement of the sensor and the measured value of the sensor. Although positioning in accordance to the Scheimflug rule is not possible for spatial reasons, which is why the working area is considerably limited, it is possible to measure with sufficient accuracy.

Preferably the radiation capacity of the projecting ray is controlled in such as way that the observing ray generates an approximately constant signal, in particular a laser diode is controlled to ensure that the amplitude of the signal on a photodiode strip is approximately constant.

To increase the accuracy of the measurement it is possible to measure the intensity and/or the half intensity width of the luminous spot generated by the projection unit and which hits the receiving unit. It is possible to flag the measured value if the intensity and/or the half intensity width are not inside the normal range.

In accordance with an advantageous further development of the invention the measured values that are afflicted with a systematic error are flagged as possibly faulty and are interpreted accordingly by the subsequent evaluation routines. It is thus avoided that erroneous measured data is incorporated with the final result.

In order to improve the measuring accuracy the stray light can be measured prior to every actual measurement and compensated for when the measured value is determined.

It is advantageous if, initially, the measured object is scanned only roughly and displayed on an output device. Thereafter, certain areas are selected and precise measurements are produced for these specified areas only. This saves considerable amounts of time because it is not necessary to record the entire measured object.

Furthermore, it can be advantageous if, utilizing the rough measurement, interactive steps are implemented and all the while the actual measuring process continues to run in the background.

BRIEF DESCRIPTION OF THE DRAWINGS

One embodiment of the apparatus according to the invention is illustrated in the drawing wherein.

DETAILED DESCRIPTION OF THE INVENTION

Figure 1:
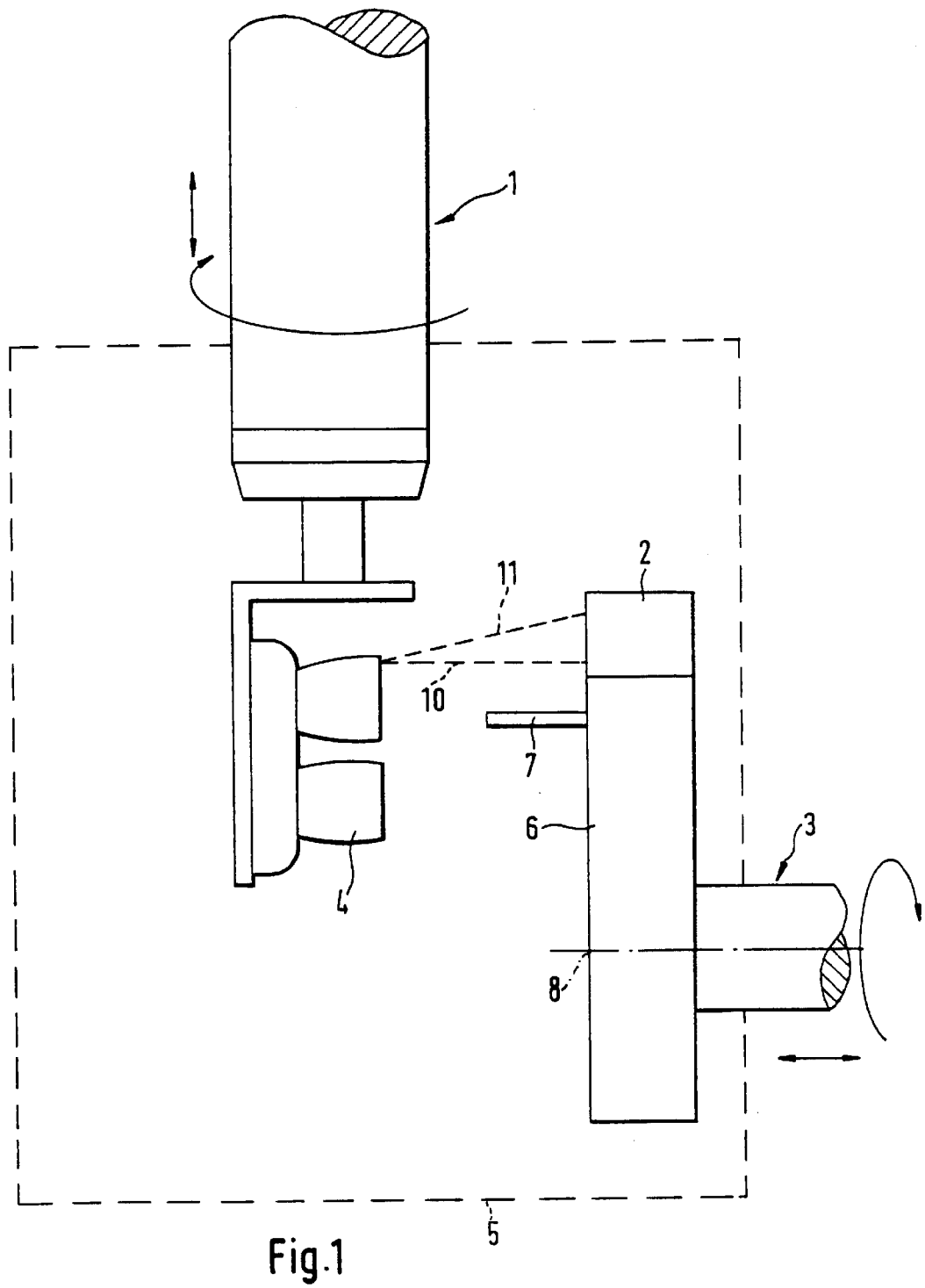
FIG. 1 is a schematic view of a sensor arranged inside a grinding chamber of grinding machine.

FIG. 1 is a schematic view of the overall apparatus of a device according to the invention in terms of an embodied example for producing a tooth restoration fitting mold.

The apparatus comprises all three of the components that are important for the production of a fitting mold, in particular a receiving unit 1, a measuring unit (sensor) 2 and a processing unit 3.

The receiving unit 1 is used, on the one hand, to receive a model of the fitting mold or of the object into which the fitting mold is to be subsequently embedded and, on the other hand (in the alternative), to receive a work piece blank of a suitable material from which the fitting mold is to be produced. The model can be either a positive or a negative model of the fitting mold or of the object.

The apparatus is shown with a positive model of a prepared tooth object 4. The receiving unit 1 allows turning and longitudinal feeding of the model.

The measuring device (sensor) 2 essentially comprises a light source producing a cleanly focussed ray of light 10 that can be aligned with the item 4, which is secured in the receiving unit 1, and of an optical receiver on which the light spot, that is projected onto the item by the ray of light 10, is imaged, represented by the projection path of the rays 10 and observation path of the rays 11.

The processing unit 3 principally comprises a spindle apparatus one end of which extends into a processing chamber 5 and is equipped there with a tool support head 6. The tool support head 6 is equipped with a tool 7 and can be moved in a longitudinal direction along the axis 8, and it can be rotated around the axis 8 which is indicated by the corresponding arrows.

Figure 2:
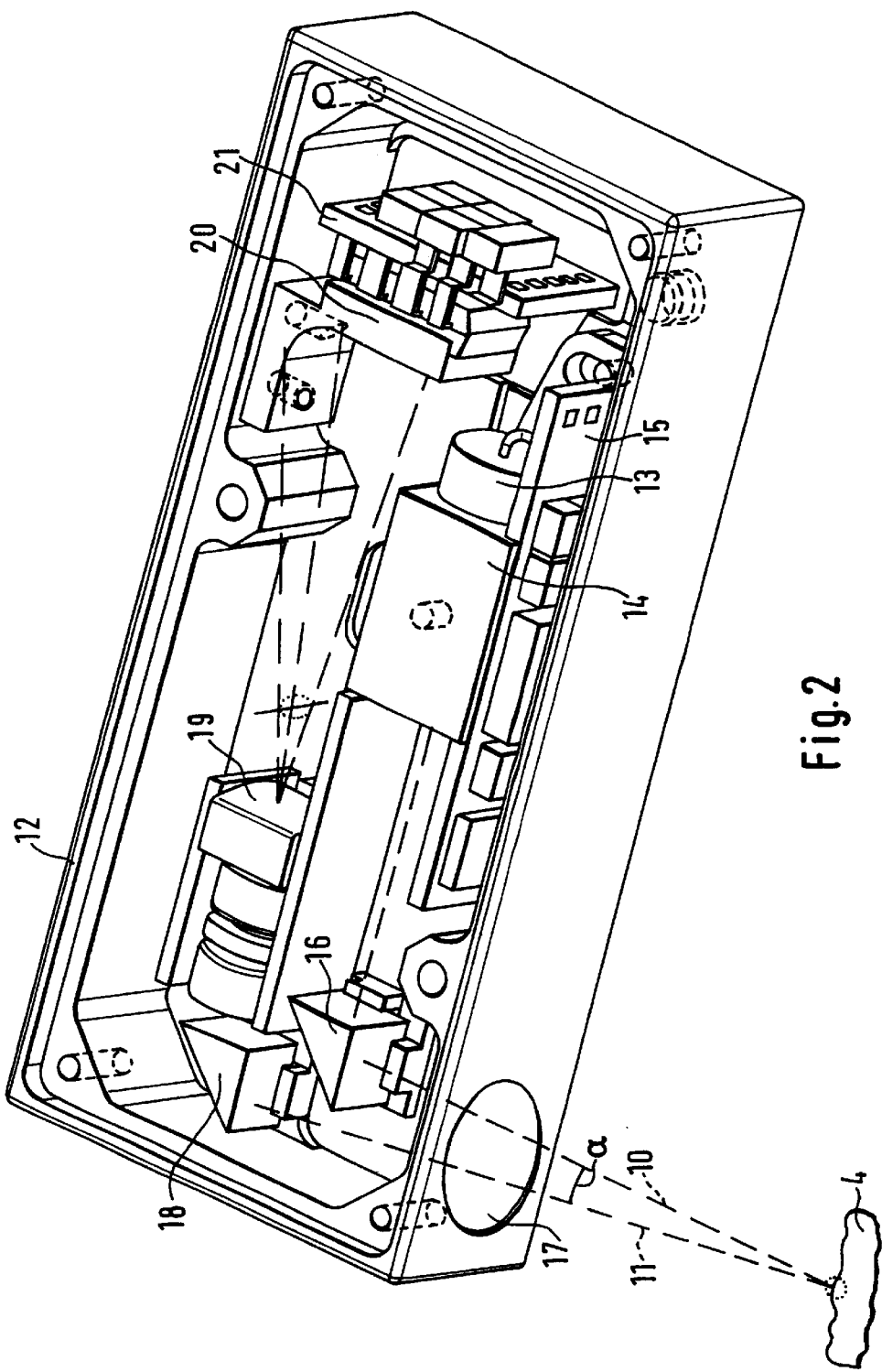
FIG. 2 is a perspective view of the sensor of the apparatus according to FIG. 1.

FIG. 2 illustrates the measuring unit (sensor) including its individual components in the form of a model construction. A laser diode 13 with a collimator optic 14 is positioned inside the housing 12 as well as a selector 15 which generates and controls the projection path of the rays.

Arranged in the projection path of the rays 10 is a prism 16 for the purpose of redirecting the beam that exits the laser diode 13 causing a redirection that is at a right angle. The laser beam leaves the housing 12 via a window 17 through which the observation path of the rays 11 is guided as well. Enclosed between the observation path of the rays 11 and the projection path of the rays 10 is the triangulation angle α which is 7° in the present case, but is preferably smaller than 5°. This triangulation angle α determines the allowable steepness of the cavity flanks of the preparations so they can still be measured with sufficient precision.

The laser beam reflected by the tooth object 4 is guided via the observation path of the rays 11 through the window 17 into the housing 12 and is redirected by the prism 18 in such a manner that the beam runs approximately parallel to the projection path of the rays.

Arranged inside the observation path of the rays 11 is a cylinder lens 19 which modifies the focus position in a plane that is perpendicular to the plane extending through the observation path of the rays and the projection path of the rays in such a way that a strip in the receiver 20 consisting of several pixels, which are arranged adjacent to each other and can be evaluated individually, is certainly located inside the range of the cone of rays.

The receiver 20 is equipped with an evaluation unit 21 allowing the measurement of the intensity and the half intensity width of the light spot, generated by the projection unit and hitting the receiving unit, as well as controlling the radiation capacity of the projection unit in such a manner that a constant signal occurs in the receiving unit. The laser diode is controlled in such a way that the amplitude of the signal is approximately constant.

Figure 3:
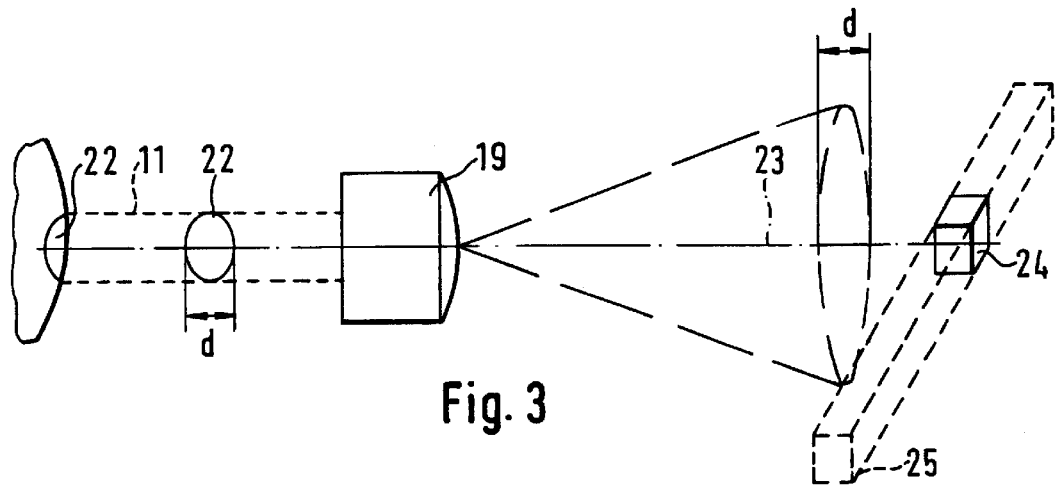
FIG. 3 is a schematic showing a divergence of the observation path of the rays in the area of the receiver.

FIG. 3 is a schematic depiction of the effect the cylinder lens 19 has with respect to the reflected luminous spot 22. The luminous spot 22 with a diameter d is generated by way of the laser beam of the projection path of the rays on the tooth object 4. It is imaged via the line 33 onto the receiving strip 25. Because of the additional use of the cylinder lens 19 a divergence in a direction that is perpendicular to the receiving strip 25 is achieved. Ideally the diameter parallel to the receiving strip remains unchanged and small. With the divergence it is prevented that pixel 24 escapes from being affected by the luminous spot 22 in case of a slight misalignment.

Figure 4:
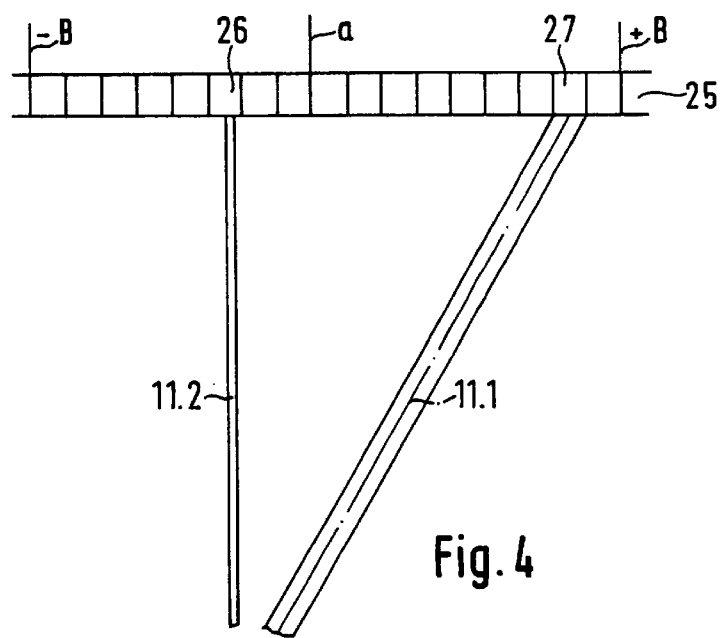
FIG. 4 is a schematic showing the position control of the sensor and the suppression of stray light.

FIG. 4 demonstrates the operation of the receiving strip 25 with different pixels that are arranged adjacent to each other. A main beam 11.1 and an auxiliary beam 11.2 hit the receiving strip 25 which is generated, for example, due to reflection on an edge of the tooth object 4. Upon evaluating the measured signal it is now possible to suppress the measured value of the pixel 26 and to take into consideration only the measured value of the pixel 27 and, if need be, of its neighbors in order to avoid any falsifications.

Moreover, FIG. 4 clarifies that a movement of the sensor toward the object or away from the object occurs if the observation path of the rays 11 reaches a previously determined outer range of the receiving strip 25 in order to ensure that the measured signals of the next step remain inside the working distance a or the range +/−B, which correspond to certain pixel ranges on the receiving strip 25, indicated by way of a, +B and −B.

What is claimed is:

1. Apparatus for recording medical objects, said apparatus comprising a position-sensitive sensor which is movable in a projection direction and includes a projection unit and a receiving unit, and between a projection path of rays of the projection unit and an observation path of rays of the receiving unit there is a predetermined triangulation angle, and the projection path of the rays is aligned parallel to the direction of movement of the sensor wherein the triangulation angle is smaller than 5°, wherein the receiving unit comprises a strip of several pixels that are adjacent to each other and can be evaluated individually acting in conjunction with a signal processing and wherein inside the observation path of the rays there are media arranged for diverging the beam in a direction that is perpendicular in relation to the receiving strip.

2. Apparatus as claimed in claim 1 wherein additional media are arranged inside at least one of the projection path of the rays and the observation path of rays for the purpose of redirecting the path of the rays.

3. Apparatus as claimed in one of the claim 1 or 2 wherein the measuring range of the sensor amounts at the most to one tenth of the largest possible object dimensions in the projection direction that is to be measured.

4. Apparatus as claimed in claim 3 wherein the projection unit comprises a laser diode with a collimator optic and a selector of the laser diode, and in particular radiation capacity is controlled by way of a PWM selector whose duty factor of pulses is calculated based on the signal of the receiver.

5. A method for the measurement of medical preparations, said method comprising the steps of:

implementing said measurement in accordance with triangulation procedure and at a predetermined triangulation angle α of less than 5°, said triangulation angle α being located between a projection path of rays and an observation path of rays;

moving a sensor by a drive apparatus in a projection direction so that an object to be measured is brought inside a range which is part of a working distance;

moving the sensor along the object that is to be measured;

checking a measured signal generated by the sensor to determine whether the signal is inside the range in relation to the working distance;

modifying the position of the sensor to the extent necessary in order to essentially reach the working distance, if the measured value is outside of the range; and producing a measured value following the subsequent calculation of the object position based on the position of the sensor and the measured value of the sensor.

6. Method as claimed in claim 5 wherein radiation capacity of the projection ray is controlled so that the observation ray generates an approximately constant signal by controlling a laser diode so that an amplitude of the signal on a photodiode strip is approximately constant.

7. Method as claimed in one of the claim 5 or 6 wherein an intensity and/or half intensity width of a luminous spot hitting a receiving unit is measured and that a measured values are flagged if the intensity and/or the half intensity width fail to be inside a normal range.

8. Method as claimed in claim 7 wherein the measured values that are afflicted with a systematic error are flagged as possibly faulty and are interpreted correspondingly in subsequent evaluation routines.

9. Method as claimed in claim 8 wherein before each measurement stray light is measured and upon determination of the measured value the stray light is compensated for.

10. Method as claimed in claim 9 wherein, initially, the measured object is scanned roughly and displayed on an output device, and wherein subsequently certain areas are selected and precise measuring is limited to the selected areas only.

11. Method as claimed in claim 10 wherein, based on a rough representation on the output device, interactive steps are implemented in order to determine the form of the restoration mold and wherein the actual measurement continues to run in the background generating continually more detailed measuring results.

* * * * *